US009920091B2

(12) United States Patent
Caulfield et al.

(10) Patent No.: US 9,920,091 B2
(45) Date of Patent: Mar. 20, 2018

(54) CONTINUOUS SYSTEM AND PROCESS FOR TREATING A LOW-WATER BIOMASS STREAM WITH LIQUEFIED-GAS SOLVENT TO SEPARATE AND RECOVER ORGANIC PRODUCTS

(71) Applicant: Green Recovery Technologies, LLC, New Castle, DE (US)

(72) Inventors: Joseph N. Caulfield, Aston, PA (US); Kenneth L. Laubsch, Mullica Hills, NJ (US); Bruce J. Rudin, Wilmington, DE (US)

(73) Assignee: Green Recovery Technologies, LLC, New Castle, DE (US)

( * ) Notice: Subject to any disclaimer, the term of this patent is extended or adjusted under 35 U.S.C. 154(b) by 0 days.

(21) Appl. No.: 15/457,450

(22) Filed: Mar. 13, 2017

(65) Prior Publication Data

US 2017/0183377 A1    Jun. 29, 2017

Related U.S. Application Data

(63) Continuation of application No. 13/804,466, filed on Mar. 14, 2013, now Pat. No. 9,651,304.

(51) Int. Cl.
| | |
|---|---|
| *C07K 1/36* | (2006.01) |
| *F26B 5/00* | (2006.01) |
| *B01D 11/02* | (2006.01) |
| *B01D 3/00* | (2006.01) |
| *C11B 3/00* | (2006.01) |
| *B01D 33/06* | (2006.01) |
| *B01D 21/02* | (2006.01) |
| *C02F 1/00* | (2006.01) |
| *C11B 1/10* | (2006.01) |

(Continued)

(52) U.S. Cl.
CPC ............... *C07K 1/36* (2013.01); *B01D 3/00* (2013.01); *B01D 11/02* (2013.01); *B01D 11/0288* (2013.01); *B01D 11/0292* (2013.01); *B01D 21/10* (2013.01); *B01D 33/06* (2013.01); *C02F 1/00* (2013.01); *C11B 1/02* (2013.01); *C11B 1/10* (2013.01); *C11B 3/008* (2013.01); *C11B 13/00* (2013.01); *F26B 5/005* (2013.01); *C02F 2001/007* (2013.01); *C02F 2101/32* (2013.01)

(58) Field of Classification Search
CPC ...... F26B 5/005; F26B 2200/02; B01D 11/02; B01D 11/0203
USPC ................................................... 34/354, 357
See application file for complete search history.

(56) References Cited

U.S. PATENT DOCUMENTS 4,223,449 A * 9/1980 Bodle .................... B01D 12/00
                                                                  208/403
4,308,200 A * 12/1981 Fremont ............ B01D 11/0203
                                                                  162/63

(Continued)

*Primary Examiner* — David J Laux
(74) *Attorney, Agent, or Firm* — James M. Lennon; Devlin Law Firm LLC

(57) ABSTRACT

A method and system for the treatment of a biomass stream to separate organic extracts/biomolecules (such as proteins, lipids and/or carotenoids) from the biomass stream, wherein the water content of the biomass stream is decreased by bringing the biomass stream into contact with a compressed liquefied gas solvent, to create a low-water content biomass stream and introducing the low-water content biomass stream to an extraction apparatus that recovers one or more organic products with little or no measurable solvent residue.

20 Claims, 1 Drawing Sheet

Process Flow Diagram

(51) Int. Cl.
    *C02F 101/32*     (2006.01)
    *C11B 1/02*     (2006.01)
    *C11B 13/00*     (2006.01)

(56) References Cited

U.S. PATENT DOCUMENTS

| | | | | |
|---|---|---|---|---|
| 4,696,114 | A * | 9/1987 | Duval | F26B 7/00 |
| | | | | 134/10 |
| 7,192,490 | B1 * | 3/2007 | Lumia | B01D 11/0203 |
| | | | | 134/16 |
| 2006/0086664 | A1 * | 4/2006 | Wills | B01D 11/0223 |
| | | | | 210/634 |
| 2011/0005125 | A1 * | 1/2011 | Adani | B01D 11/0203 |
| | | | | 44/605 |

* cited by examiner

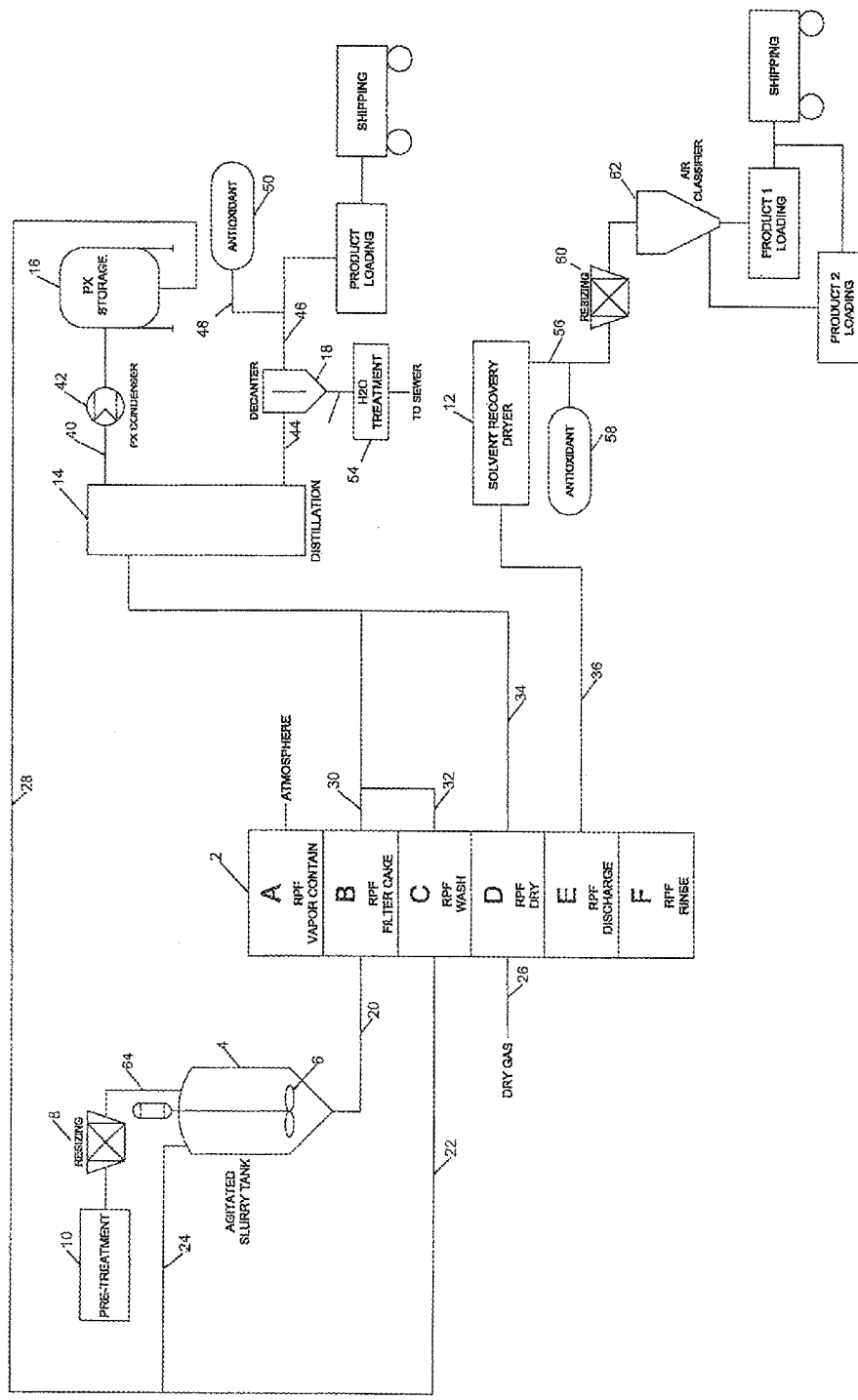

CONTINUOUS SYSTEM AND PROCESS FOR TREATING A LOW-WATER BIOMASS STREAM WITH LIQUEFIED-GAS SOLVENT TO SEPARATE AND RECOVER ORGANIC PRODUCTS

CROSS-REFERENCE TO RELATED APPLICATION

The present application is a continuation of currently pending U.S. Utility application Ser. No. 13/804,446, filed Mar. 14, 2013, which is hereby incorporated by reference herein in its entirety.

BACKGROUND OF THE INVENTION

Field of the Invention

The invention relates to a method for dewatering and separating animal process wastewater, vegetable and fruit waste and other industrial and municipal waste and post-waste streams using a liquefied gas solvent in a rotary pressure filter to yield one or more proteins, lipids and/or other useful biomass extracts.

Description of the Related Technology

Various types of separation and extraction processes are employed to recover materials dissolved or suspended in waste streams. Many separation methods, solvents, gases and apparatus exist to separate different types and volumes of biomass into useful by-products with a wide range of values, from commodities to value added ingredients. In the animal processing waste product industry, dissolved air flotation and other flocculation processes with or without some combination with centrifuge processes are used most often to separate saleable by-products, such as lipids, from the animal processing wastewater streams. However, much of the value in lipids and proteins remain in the post-flocculated material commonly known as "DAF" ("DAF" is an acronym for "dissolved air flotation" and sometimes also is used in reference to the resulting material after dissolved air flotation processing). While poultry, beef, pork, dairy and fish waste streams respond differently to flocculation and centrifuge processes, significant quantities of valuable by-products still remain in the waste stream. By contrast, fruit, vegetable and other botanical matter may employ different processes for recovering saleable by-products which apply extensive heat and pressure to produce certain extracts, although the heat and pressure can damage the resultant products in ways that limit usefulness and therefore their value.

Others have described methods and systems to process "DAF" and other waste materials. For example, U.S. Pat. No. 7,186,796 provides a method of isolating a bio-molecule including peptides, proteins, polynucleotides and polysaccharides from a water-borne mixture by contacting the water-borne mixture with dimethyl ether to precipitate solid particles of the bio-molecule. The water-borne mixtures include aqueous solutions, suspensions, emulsions, microemulsions and liposomes suspended in aqueous media. Similarly, U.S. Pat. No. 7,897,050 provides a method and system for the extraction of an organic chemical constituent, including hydrocarbons, crude petroleum products, refined petroleum products, synthetic compounds from a solid matter, including from animal renderings, using an inclined auger in a pressurized chamber. Thus, prior art systems have focused on higher value input streams, and generally worked with smaller volumes of waste materials where the methods, apparatus and chemistry can yield a higher value output. Prior art has been limited by the cost to scale the process in the form of cost prohibitive capital equipment needed to process large volumes of waste streams and/or the operating cost in the form of energy required to separate the waste streams into valuable commodity products.

In principle, continuously and discontinuously operating pressing apparatuses, e.g. multi-platen presses, strainer presses, plate filter presses, travelling screen presses and screw presses, are suitable for separating off the lipids and proteins from the biomass. Centrifuges are likewise suitable for separating off lipids from the biomass. Known types of centrifuges include, for example, turnout centrifuges, peeler centrifuges, pusher centrifuges, mesh screw centrifuges, vibrating centrifuges and sliding centrifuges and decanters. See, e.g., WO 2010/001492 A1, relating generally to recovering tallow and more particularly, to removing fats, oil and grease and recovering tallow from food or animal processing wastewater by adding a flocculant and separating the tallow from the solids employing a centrifuge.

A further method which has attained importance for separating lipids and proteins from a biomass is filtration. A distinction is made between discontinuous and continuous filtering systems. Discontinuously operating filters include, for example, fixed-bed filters, suction filters, candle filters, leaf filters and plate filters. The separation of lipids and protein from the biomass by means of discontinuously operating filters is generally less preferred. A disadvantage here is the loading and unloading of the filter, which requires a considerable time, as well as filter clogging related to lipid viscosity exacerbated by lower processing temperatures where liquefied gases are employed. It is a further disadvantage that DAF, in aqueous solution, yields flux rates that make traditional commercial filters unusable. Thus, discontinuously operating filters are not suitable for large biomass throughputs. Large biomass throughputs can be categorized as several tons of input waste per hour.

Continuously operating filters, such as belt filters and rotary filters, also have been found to be useful as separation apparatuses, and rotary pressure filters as are known from WO 02/100512 A1 are particularly suitable.

Generally, solvent extraction can be used to increase the yield of recovered lipids 5173763 and protein from biomass waste streams. However, solvent extraction produces a solvent-extracted residue which contains residual solvent. Consequently, there is a need for a method for separating lipids and proteins from biomass waste streams providing a useful product having an acceptably low residual solvent content and correspondingly low toxicity effects.

There remains a need to create energy- and economically-efficient systems to extract solutes such as lipids and proteins from post waste biomass materials, such as animal "DAF", flocculated and nonflocculated animal, vegetable and fruit wastestreams and other matter. The present invention addresses these and other needs.

BRIEF SUMMARY OF THE INVENTION

In one embodiment, the invention relates to a method of extracting and separating a bio-molecule from partially or substantially dewatered biomass. The biomass comprising proteins and desired bio-molecules, such as lipids and/or carotenoids, may first be introduced into an agitator vessel where it is mixed with a liquefied gas solvent. The biomass next is passed into a rotary pressure filter (RPF) and deposited into individual filter cells of the RPF by rotating the RPF drum. While in the individual filter cells and in the wash zone of the RPF, the biomass is contacted with additional liquefied gas solvent. The desired bio-molecules (such as but not limited to lipids) are separated from the biomass by passing the solvent through the biomass containing filter cells to obtain a solvent and bio-molecule stream through the cylindrical vessel of the RPF. In this way, bio-molecules (such as lipids) and remaining water from the biomass are extracted from the biomass, and the protein is retained in the individual filter cells as a result of the separation. The individual filter cells contain a cake of accumulated protein that is substantially moisture free and can be discharged from the RPF. Solvent may remain in the accumulated protein requiring subsequent solvent removal in a further step.

In some embodiments, the biomass is pretreated in a dewatering process before it is introduced into either an agitator vessel or into the RPF. The pretreatment or dewatering process may comprise mixing the wastewater stream to normalize the input, contacting the biomass with one or more solvents, or by the application of thermal energy and recovering the water and solvent. The solvent of the pretreatment may comprise additional quantities of the same liquefied gas solvent used within the rotary pressure filter.

In some embodiments, the method further comprises conveying the liquefied gas solvent, water and bio-molecules (such as lipids) to a distillation system where the constituents are separated. The distilled solvent is re-condensed, recovered and conveyed back into the system for re-use, either in the pretreatment unit or in the rotary pressure filter. Where the bio-molecules are lipids, the lipids may further be treated with an antioxidant to prevent spoilage, the treatment occurring, for example, after pretreatment and/or after distillation. The lipids may thereafter be stored in a vessel to be transported for sale. The water is separated using any suitable method known in the art and stored for disposal or re-use.

In some embodiments, the method further comprises mechanically filtering the dry protein, and storing the filtered protein for transportation and sale. Minimal dry waste from the protein filtration process is stored for transportation to disposal.

Another embodiment comprises a system for extracting and separating a bio-molecule from biomass. The system includes a rotary pressure filter with a plurality of individual filter cells distributed on a rotational drum of the rotary pressure filter adapted to receive a mixture or slurry of a biomass with at least one liquefied gas solvent, and with at least one chamber through which liquefied gas solvent may be introduced so as to filter through the mixture or slurry held within the filter cells to extract desired bio-molecule(s) and leave a filter cake comprising primarily protein in each filter cell. In a preferred embodiment, a heater preheats the biomass to a temperature above room temperature before introducing the biomass into the rotary pressure filter. In yet another preferred embodiment, desired bio-molecules (such as lipids) extracted from the biomass and the liquefied gas solvent are recovered via at least one distillation column.

In some embodiments, the biomass is plant matter, such as but not limited to, soybean, rapeseed, canola, camolina, corn, sunflower, palm, jatropha, corn germ, distillers grains, safflower, cottonseed, flax, peanut, sesame, olive and/or coconut. The biomass also can be nuts and/or seeds, or can be other fruit and/or vegetable matter. In some embodiments, the biomass is algae.

The biomass also can be the waste stream that comes from vegetable processing for example from carrots, kale, or tomato processing. In other embodiments the biomass is water saturated hydrocarbon wastestreams or activated sludge that comes from industrial or municipal wastewater processing.

In some embodiments, the biomass is animal matter, such as but not limited to 5173763 animal by-products from a meat processing plant or by-products of wastewater from a protein processing facility. Usually, the animal matter is inedible by humans but edible to domesticated animals (e.g., canines or felines), or farm animal feed or is waste from the processing of edible animal matter. In some embodiments, the animal matter is from, for example, avian (e.g., chicken, turkey, duck, goose, ostrich, emu), porcine, bovine, ovine (e.g. lamb, sheep or goat), deer (i.e., venison), buffalo and/or fish slaughter, hatchery or meat processing. In some embodiments, the animal matter is beef rendering, chicken rendering, pork rendering, or fish rendering effluent. In some embodiments, the animal matter is poultry, pork, beef, veal, lamb and/or mutton. In further embodiments, the animal matter is a flocculated or nonflocculated effluent wastewater stream from an animal processing plant, such as from poultry, beef, pork, fish and dairy processing, or the waste that arises from poultry hatchery operations, such as spent/unfertilized/broken eggs, deceased chicks or the fines that arise out of feed processing for all animal sources. In further embodiments, the animal matter may be dairy waste, such as spilled or spoiled milk.

Suitable solvents comprise liquified gases. In some embodiments, the liquefied gas solvent is selected from butane, isobutane, propane, carbon dioxide, dimethyl ether, methane, ethane, nitrous oxide, propylene, isobutene, ethylene, sulfur hexafluoride, ammonia, gaseous hydrocarbons, gaseous halogenated hydrocarbons, fluorocarbons, sulfur dioxide, and mixtures thereof. Alternatively, co-solvents such as low molecular weight alcohols, blended dimethyl ether and/or ethanol may be used. Suitable co-solvents include, but are not limited to ethanol, propanol, isopropyl alcohol, 2-methyl-2-propanol and mixtures thereof.

DESCRIPTION OF THE DRAWING

Other aspects and advantages will be apparent from the following description given hereinafter referring to the attached drawing.

FIG. 1 is a simplified process flow diagram of biomass separation and extraction process.

DETAILED DESCRIPTION OF PREFERRED EMBODIMENTS

Rotary pressure filters are known in industry for separating suspensions, such as cellulose products, intermediate plastic products, organic chemicals, agrochemicals, instant coffee, starch, pharmaceuticals and dyes/pigments. A rotary pressure filter is a continuously operating filter having a pressure-tight design. It consists essentially of a metallic filter drum that rotates at a regulated continuous speed, an associated control head, and a metallic, pressure-rated housing. The annular space between the filter drum and the housing is sealed at the sides by means of stuffing boxes or other sealing systems. The housing is divided radially into pressure-tight chambers by means of zone separators which are held at a constant force against the drum. The surface of the drum comprises individual filter cells which are connected via outlet tubes to the control head. A detailed description of a representative rotary pressure filter may be found in WO 02/100512 A1.

When using a rotary pressure filter, a suspension to be filtered is fed continually under a constant admission pressure into the filtration zone of the rotary pressure filter and into individual filter cells. A filter cake is built up in each of the filter cells of the rotating drum. The filter cake is then conveyed into the subsequent chambers of the rotary pressure filter for after-treatment, e.g., washing and/or treatment with steam, an inert drying gas or heated solvent gas. The filter cake is taken off in an unpressurized zone of the filter either by means of an automatically operating, adjustable, mechanical scraper or/and by means of a targeted reverse pulse, typically of compressed air, nitrogen or steam. A description of the zone separators for one example of a rotary pressure filter is provided in WO 02/100512 A1.

Heretofore, rotary pressure filters have not been used to process biomass materials. Disclosed herein is a method of extracting and separating a bio-molecule, such as a lipid and/or a protein, from partially dewatered or substantially dewatered biomass that includes the step of contacting the biomass with compressed liquefied gas solvent while the biomass is held within individual filter cells in a rotary pressure filter. After the biomass is contacted with the compressed liquefied gas solvent, a continuous stream of extracted desired bio-molecules (such as lipids) is entrained in a solvent stream that is directed out of the rotary pressure filter, and a filter cake of protein is left in each filter cell. The invention provides a robust, scalable, low-cost process for separating water and desired bio-molecules (such as lipids) from the protein(s) of a partially dewatered or substantially dewatered biomass while maintaining desired characteristics of the protein(s) and lipids extracted.

Applicants have found that compressed gas solvents are advantageous for extracting and separating lipids from partially dewatered or substantially dewatered biomass using a rotary pressure filter. In some embodiments, the liquefied gas solvent is selected from butane, isobutane, propane, carbon dioxide, dimethyl ether, methane, ethane, nitrous oxide, propylene, isobutene, ethylene, sulfur hexafluoride, ammonia, gaseous hydrocarbons, gaseous halogenated hydrocarbons, fluorocarbons, sulfur dioxide, and mixtures thereof. In some embodiments, the liquefied solvent gas is dimethyl ether, butane or propane. Alternatively, co-solvents such as low molecular weight alcohols, blended dimethyl ether and/or ethanol may be used. Suitable co-solvents include, but are not limited to, ethanol, propanol, isopropyl alcohol, 2-methyl-2-propanol or mixtures thereof.

One preferred compressed liquefied gas solvent is liquid dimethyl ether. Dimethyl ether (also known as methyl ether) is soluble in water, and also dissolves water. This solubility is maintained along the entire vapor-pressure curve of dimethyl ether from about −5° C. to above its critical temperature ($T_c$) of 126.9° C.

A biomass may be collected from any suitable source. For example, if the biomass is plant matter, agricultural waste or food processing waste may be collected. If the biomass is animal matter, agricultural waste or meat processing waste may be collected. The biomass as collected may comprise up to 20 to 85% water with the remainder being suspended or dissolved solids and any impurities that may exist in the waste stream.

To achieve maximum yields of the desired products, including for example lipids and proteins when processing a biomass, and at the same time maximize economic efficiency of the process, it is contemplated that a partially dewatered or substantially dewatered biomass be used. For a substantially dewatered biomass, the percentage of water is less than about 20% by mass or less. Preferably, the water content of the biomass entering the rotary pressure filter is less than 10% by mass, and most preferably less than 5% by mass.

To achieve maximum processability of the biomass and improve economic efficiency, in one embodiment, the biomass is continuously mixed in a suitably pressurized agitation vessel 4 with solvent, where the ratio of solvent to biomass is 5:1. A ratio of 4:1 is preferred, and a ratio of 3:1 is most preferred. It is understood that the actual water percentages and solvent to biomass ratios employed are those that ensure that the mixture is still flowable or movable to be introduced into a rotary pressure filter for next processing steps.

A suitable pressurized agitation vessel 4 includes, for example, a stirred tank 4 with a multi-blade impeller 6 that rotates at speeds from about 40 to about 320 revolutions per minute (see FIG. 1). The vessel interior preferably is maintained at pressures above atmospheric pressure, such as 3 to 9 bar (gage).

FIG. 1 shows one embodiment of a simplified process flow diagram of a method or process and system that can be used to separate and extract lipids and proteins from a biomass. Referring to FIG. 1, a pre-treatment unit 10 for the biomass is connected to a resizing unit 8 which is connected via a biomass supply line 64 to a pressurized agitator vessel 4 with an agitator or impeller 6. The biomass is agitated to form a slurry with a liquefied gas solvent in the agitator vessel 4.

From the agitator vessel 4 the biomass slurry is introduced into a rotary pressure filter 2. The agitator vessel 4 has at the tank inlet a solvent pipeline 24, and at the tank outlet, a pipeline 20 connected to the rotary pressure filter 2. The rotary pressure filter 2 shown in FIG. 1 is sub-divided into six working chambers A-F. The system in FIG. 1 also includes a solvent recovery dryer 12 and a distillation column 14.

From the rotary pressure filter 2, filtrate lines 30 and 32 lead to a distillation column 14. In addition, the rotary pressure filter 2 has a solvent inflow pipeline 22, an inflow line 26 for drying gas, such as Nitrogen (N2) or superheated DME vapor and an outflow line 34 for the drying gas, and a discharge chute 36 for the filter cake. Optionally, a dryer dries the filter cakes before the filter cakes are removed from each filter cell.

The discharge chute 36 is connected to the solvent recovery dryer 12. After removing any remaining solvent from the protein, the protein is discharged via a discharge chute 56 to an air classifier 62 via resizing unit 60. Leaving the outlet of the air classifier 62, the protein is transferred to packaging or other desired storage or to shipping.

The filtrate containing solvent, desired bio-molecules (e.g., lipids) and water is provided via lines 30, 32 and 34 to the distillation column 14, from which the solvent gas is removed via outlet line 40 provided with a solvent condenser 42 for the solvent. The recovered liquefied solvent is stored in solvent storage container 16 and, via pipeline 28, connected with supply line 24 to the agitator vessel 14 and with supply line 22 to the rotary pressure filter 2.

The distillation column 14 outlet is connected via outlet line 44 to a lipid/water separation unit 18, such as a decanter, from which water is removed via outlet line 52 to a water treatment unit 54. From the top of the separation unit 18, desired bio-molecules (e.g., lipids) are removed via pipeline 46 provided with antioxidant from an antioxidant storage tank 50 via pipeline 48 to packaging or other desired storage or to shipping.

The extraction and separation sequence proceeds in one preferred embodiment as 5173763 follows with reference to FIG. 1: A biomass is collected from a suitable source. The biomass optionally is pretreated in pre-treatment unit 10 to remove some water. Pretreatment may include supplying thermal energy to the biomass or supplying a co-solvent to the biomass. If thermal energy is supplied to the biomass, the water content may be reduced to a level below about 20% by mass. The biomass is then supplied to the pressurized agitator tank 4 via line 64. Liquefied gas solvent also is supplied to said tank via line 24. The agitator or impeller 6, set at a rotational speed suitable for the biomass, stirs the biomass to form a mixture or slurry and ensures consistency of the biomass/solvent mixture. The mixture or slurry remains in the agitator vessel for a time sufficient to provide intimate contact between the solvent and the bio-molecules (e.g., lipids). It will be readily apparent that the mixing time varies depending on the size of agitator vessel and the flow rate of the solvent used.

The biomass/solvent mixture or slurry next is transferred from the agitator vessel 4 under constant pressure through a port 20 and into working chamber B of the rotary pressure filter 2, where the biomass mixture or slurry is deposited into the individual filter cells distributed on the rotary pressure filter's rotational drum, forming a filter cake in each filter cell. As a result of the rotary movement of the filter drum, the filter cells with the filter cakes are conveyed into working chamber C. Additional liquefied gas solvent, such as pressurized dimethyl ether or other liquefied gas solvent, is supplied to working chamber C. While a filter cake composed of protein and possibly other non-dissolvable material is forming within each of the filter cells, the filtrate, which consists principally of the remaining water and extracted bio-molecules (e.g., lipids), and solvent obtained in working chambers B and C of the rotary pressure filter by washing the biomass with the liquefied solvent, is let out of the rotary pressure filter through filtrate lines 30 and 32 and introduced into a distillation column 14. Following the washing and lipid extraction processes in chambers C and B, residual solvent content and moisture, if necessary, is adjusted in chamber D to reduce the load on subsequent processing steps. For this purpose, a drying gas at a pressure of 6 bar (gage) is supplied though inlet line 26 to drying chamber D and let out though outflow line 34 to the distillation column 14. As a result of further rotation of the filter drum, the filter cells with the dry filter cakes therein are conveyed into working chamber E where the filter cakes are forced out of the filter cells using a back pulse gas alone or in combination with a knife blade and conveyed out of the rotary pressure filter. After removal from the filter cells and the drum of the rotary pressure filter, the filter cakes, consisting of protein and any remaining solids, are taken off though the discharge chute 36 and introduced into a solvent recovery dryer 12.

In filter chamber F the filter cells are washed off to remove residual proteins and filter cake residues from the filter cells. Chamber A functions as a vapor containment zone where any gas escaping the process is captured and either discharged or recycled.

The filtrate containing solvent, extracted bio-molecules (such as lipids) and water is provided via lines 30, 32 and 34 to inlet to the distillation column 14. Overhead, the liquefied gas solvent is removed via outlet line 40 and liquefied in condenser 42. The liquefied gas solvent is stored in solvent storage container 16. From solvent storage container 16 the liquefied gas solvent may be recycled and returned for re-use via pipeline 28, connecting with supply line 24 to the agitator vessel 4 and with supply line 22 to the rotary pressure filter 2. Water and bio-molecules (such as lipids) are removed from the bottom of the column 14. Lipids and water are separated in lipid/water separation unit 18 or decanter. The lipids may be treated with an antioxidant to prevent spoilage, and stored for further processing, or may be loaded and shipped. A palatability enhancer and/or a stabilizing agent may be added to the proteins. Proteins also may be sifted for particle size classification.

The pre-treatment facility 10 optionally may be located at the same site as the rotary pressure filter 2 and other equipment for extraction and separation.

EXAMPLES

Example 1

Seven (7) tons of Chicken DAF from a medium scale poultry operation are collected and pumped through the pretreatment process at a rate of 7 wet tons per hour. The solids content of the incoming DAF is on average 30% solids and 70% moisture. The moisture content after pretreatment is on average less than 2% moisture. To render the material according to the specification of the pet food industry, the material is heated to a temperature of 140° C. temperature for a minimum of 20 minutes. The resultant sludge is stored in 1 ton containers for further processing.

The sludge is processed for particle size reduction in a Macerator, obtainable from Vogelsang, to facilitate pumping into the slurry mixing tank. The processed sludge is introduced into the slurry mixing tank (e.g., Silverson Rotor/Stator Mixer) at a rate of 2 tons per hour. The slurry tank pressure is held at 6 bar. The impeller speed is set at 8000 rpm. The solvent, liquified dimethyl ether (DME), supplied by Diversified CPC International, is added at a ratio of 3:1 by mass to the incoming sludge. Mixing and particle size reduction is achieved through the use of a stator/rotor mixing element with an impeller speed of 8000 rpm. Further particle size reduction may be achieved through the use of an inline mixer with a speed of 8000 rpm.

The well mixed sludge/solvent solution is then metered across a control valve to maintain a constant mass flow to the slurry inlet zone of the Rotary Pressure Filter (RPF), obtainable from BHS-Filtration Inc., Model A6. Upon entering the RPF, the sludge/slurry mixture passes through a peek filter cloth element approximately 50 micron in opening size. The solids are deposited on the filter cloth, creating a cake thickness anywhere between 7 and 30 mm.

The cake then rotates out of the slurry inlet zone and enters the wash zone where the cake is introduced to pure liquefied DME solvent at a ratio of 2:1 based on sludge mass. The clean solvent passes through the cake and further extracts lipids and moisture.

The slurry and wash filtrate is then stored and sent to a single distillation column for further refinement. The solvent is evaporated and collected at a purity greater than 99%. The remaining moisture and lipids pass through one distillation at a maximum temperature of 140° C. and are further separated by either standard decantation or a centrifuge. The resulting lipids have a moisture content of below 0.5%. The retained solvent in the lipids is below the 1 parts per million detectable level. Finally, the lipids are filtered in a 1 micron polyester filter cartridge, obtainable from McMaster, to remove solid particulate prior to packaging and shipment.

The protein stream leaves the RPF wash zone and goes to the RPF dry zone where nitrogen gas is passed through at a volume exchange ratio of approximately 10:1. This removes solvent down to 100% or less hold up. The drying gas is then passed through a compressor and condenser to collect the solvent for reuse.

The protein stream leaves the drying zone of the RPF and discharges to 0.5 bar 5173763 discharge zone where it is removed from the RPF via scraper blade, purge gas, or both. It then travels through a pressure isolating rotary valve into a solvent dryer operating at 2 bar and a maximum temperature of 350° F. A drying gas, such as nitrogen, is passed over the protein at a ratio of 2:1 solvent to drying gas. The drying gas is then sent to a compressor and the solvent is condensed to recycle the solvent. The protein, free of solvent down to below parts per million level, is discharged from the solvent dryer through a rotary valve. From there, the protein is conveyed and may be passed through a particle size classifier so that it may be sold according to grade and product specification. In addition, stabilizing agents, such as PE-TOX from Kemin Industries (believed to be a mixture of butylated hydroxyanisole (BHA) and butylated hydroxytoluene (BHT)) or NATUROX from Kemin Industries (believed to be a mixture of tocopherol(s) with lecithin), are added to stabilize the lipid content in the protein. The lipid content in the protein stream is typically 8%.

Example 2

Seven (7) tons of carrots are obtained from a carrot processing plant. The solids content of the carrots is on average 13.5% solids, and the moisture content is 85%. Using a Comitrol® processor available from Urschell, the carrots are resized to facilitate pumping into the slurry mixing tank. The carrot sludge is introduced into the slurry mixing tank at a rate of 3 tons per hour. The slurry tank pressure is held at 6 bar. The solvent and co-solvent, liquified dimethyl ether (DME), supplied by Diversified CPC International, and ethanol, supplied by Sigma Aldrich, are added at a total solvent ratio of 3:1 by mass to the incoming sludge. The ratio of DME to ethanol is 1:10. Mixing and particle size reduction is achieved through the use of a stator/rotor mixing element with an impeller speed of 8000 rpm. Further particle size reduction may be achieved through the use of an inline mixer at a speed of 8000 rpm.

The well mixed sludge/solvent solution is then metered across a control valve to maintain a constant mass flow to the slurry inlet zone of a Rotary Pressure Filter from BHS-Filtration Inc., Model A6. Upon entering the RPF, the sludge/slurry mixture passes through a PEEK filter cloth element approximately 50 micron in opening size. The solids are deposited on the filter cloth creating a cake thickness anywhere between 7 and 30 mm. The cake then rotates out of the slurry inlet zone and enters the wash zone where the cake is introduced to pure liquefied DME and ethanol at a total solvent ratio of 1:1 based on sludge mass. The clean solvent passes through the cake and further extracts lipids and moisture.

The slurry and wash filtrate is then stored and sent to a single distillation column for further refinement. The solvent is evaporated and collected at a purity greater than 99%. The remaining moisture and lipids pass through two distillation columns at a maximum temperature of 80° C. and are further separated by either standard decantation or a centrifuge. The resulting lipids have a moisture content of below 0.5%. The retained solvent in the lipids is below 10 parts per million level. Finally, the lipids are filtered in a 1 micron filter cartridge to remove solid particulate prior to packaging and shipment.

The protein stream leaves the RPF wash zone and goes to the RPF dry zone where 5173763 nitrogen gas is passed through at a volume exchange ratio of approximately 10:1. This removes solvent down to 100% or less hold up. The drying gas is then passed through a compressor and condenser to collect the solvent for reuse. The protein stream leaves the drying zone of the RPF and discharges to 0.5 bar discharge zone where it is removed from the RPF via scraper blade, purge gas, or both. It then travels through a pressure isolating rotary valve into a solvent dryer operating at 2 bar and a maximum temperature of 350° F. A drying gas is passed over the protein at a ratio of 2:1 solvent to drying gas. The drying gas is then sent to a compressor and the solvent is condensed to recycle the solvent. The protein, free of solvent down to below 10 parts per million level, is discharged from the solvent dryer through a rotary valve. From there, the protein is conveyed and may be passed through a particle size classifier so that it may be sold according to grade. In addition, stabilizing agents, such as PE-TOX from Kemin Industries (believed to be a mixture of butylated hydroxyanisole (BHA) and butylated hydroxytoluene (BHT)) or NATUROX from Kemin Industries (believed to be a mixture of tocopherol(s) with lecithin), are added to stabilize the lipid content in the protein. The lipid content in the protein stream is typically 8%.

Numerous characteristics and advantages have been set forth in the foregoing description, together with detail of structure and function. The novel features are pointed out in the appended claims. The disclosure, however, is illustrative only, and changes may be made in detail, especially in matters of size, shape, and arrangement of parts, within the principle of the invention, to the full extent indicated by the broad general meaning of the terms in which the appended claims are expressed. Therefore, the invention must be measured by the claims and not by the description of the examples or the preferred embodiments.

We claim:

1. A continuous-feed method for treating a biomass stream to separate and recover from the biomass one or more organic products with little or no measurable solvent residue, comprising:
    introducing a biomass into a continuous system at atmospheric pressure, wherein the biomass is continuously fed in a stream through the system without batching;
    maintaining a water content level at or below 20% water by mass of the biomass stream by contacting the biomass with a liquefied-gas solvent, wherein the maintaining step comprises:
        contacting the biomass stream with the compressed liquefied-gas solvent;
        maintaining a pressure on the combined biomass stream and solvent during the contacting step, at a pressure that is sufficient to compress the liquefied-gas solvent;
    passing the pressurized combined biomass stream and solvents through a filter to separate the combined biomass stream and solvents into two streams: a solid, organic-extract stream, and a liquid stream;
    moving the solid, organic-extract stream away from the filter and decreasing the pressure on the solids stream as the stream moves away from the maintaining step;
    moving the liquid stream, comprising the solvent and water, away from the filter and decreasing the pressure on the liquid stream to evaporate and separate the solvent from the liquid stream; and
    collecting the extract.

2. The method of claim 1, wherein the water content level of the biomass stream is maintained at or below 5% water by mass in the maintaining step.

3. The method of claim 1, wherein the evaporated solvent is compressed and recycled back into contact with the biomass stream at the contacting step.

4. The method of claim 1, wherein the organic-extract is a protein.

5. The method of claim 4, wherein the separated protein is an essentially non-denatured, whole protein.

6. The method of claim 1, wherein the liquid stream of the moving liquid step includes a suspended biomolecule comprising a lipid or a carotenoid.

7. The method of claim 6, wherein the biomolecule is separated from the water in the moving the liquid stream step by mechanical separation.

8. The method of claim 7, wherein the separated biomolecule is a lipid and the lipid is filtered with a 1 micron filter to remove solid particulate from the lipid.

9. The method of claim 1, wherein the ratio of solvent to biomass at the contacting step is between 5:1 and 2:1.

10. The method of claim 1, wherein any residual amount of solvent retained in the separated extract is at or below 10 parts per million.

11. The method of claim 1, wherein any residual amount of solvent retained in the separated extract is at or below 30 parts per million.

12. The method of claim 1, wherein the decreasing of the pressure on the solid organic-extract stream involves a decrease to atmospheric pressure.

13. The method of claim 1, where the pressure of the maintaining step is in a range between 2 bar and 9 bar.

14. The method of claim 1, where the temperature of the liquefied-gas solvent during the maintaining step is maintained between about −5° C. and about 127° C.

15. A continuous-feed system for the continuous treatment of a biomass stream to separate from the biomass stream one or more organic products with little or no measurable solvent residue, comprising:
an inlet configured for introducing a biomass to the system at atmospheric pressure, wherein the system is configured to continuously feed the biomass in a stream through the system without batching;
a chamber, connected to the inlet by piping, configured to maintain a water level at or below 20% water by mass of the biomass stream by contacting the biomass with a liquefied-gas solvent, wherein the chamber comprises:
a solvent inlet for introducing and bringing the liquefied-gas solvent into contact with the biomass stream;
a pressure gauge and regulator for maintaining a pressure on the combined biomass stream and solvent in the chamber, at a pressure that is sufficient to compress the liquefied-gas solvent;
a filter configured to separate the pressurized and combined biomass stream and solvents passing through the filter into two streams, a solid, organic-extract stream and a liquid stream;
a conveyor configured to move the solid, organic-extract stream away from the filter and configured to decrease the pressure on the solids stream as the stream flows away from the chamber;
a conveyor configured to move the liquid stream, comprising the solvent and water, away from the filter and configured to decrease the pressure on the liquid stream to evaporate and separate the solvent from the liquid stream; and
a collector to collect the extract.

16. The system of claim 15 further comprising a recycling loop of piping through which the evaporated solvent may be compressed and recycled back into contact with the biomass system though the solvent inlet.

17. The system of claim 15 further comprising a separator connected to the liquid stream conveyor configured to mechanically separate the liquid stream into a biomolecule and water.

18. The system of claim 17, wherein the mechanical separator is configured to separate a biomolecule that is a lipid and wherein the separator is connected to a 1 micron filter configured to remove solid particulate from the lipid.

19. The system of claim 15, wherein the pressure gauge and regulator of the chamber are configured to maintain a pressure on the biomass stream in a range between 2 bar and 9 bar.

20. The system of claim 15, wherein the chamber is configured to maintain a temperature of the biomass stream in a range between about −5° C. and about 127° C.

* * * * *